(12) United States Patent
Panasyuk

(10) Patent No.: US 8,685,092 B2
(45) Date of Patent: Apr. 1, 2014

(54) MATERIAL FOR OSTEOPLASTY AND TISSUE ENGINEERING

(76) Inventor: Andrey Fedorovich Panasyuk, Moscow (RU)

(*) Notice: Subject to any disclaimer, the term of this patent is extended or adjusted under 35 U.S.C. 154(b) by 72 days.

(21) Appl. No.: 13/572,793

(22) Filed: Aug. 13, 2012

(65) Prior Publication Data

US 2012/0308665 A1 Dec. 6, 2012

Related U.S. Application Data

(63) Continuation-in-part of application No. 12/091,741, filed as application No. PCT/RU2005/000526 on Oct. 27, 2005, now Pat. No. 8,241,673.

(51) Int. Cl.
*A61F 2/28* (2006.01)
*C08L 89/00* (2006.01)

(52) U.S. Cl.
USPC ............. 623/16.11; 106/160.1; 514/801

(58) Field of Classification Search
USPC ............. 623/16.11; 106/160.1; 514/801
See application file for complete search history.

(56) References Cited

U.S. PATENT DOCUMENTS

| | | | |
|---|---|---|---|
| 4,394,370 A | | 7/1983 | Jeffries |
| 4,627,853 A | | 12/1986 | Campbell |
| 4,743,259 A | | 5/1988 | Bolander |
| 5,585,116 A | * | 12/1996 | Boniface et al. ............. 424/549 |
| 5,728,159 A | | 3/1998 | Stroever et al. |
| 6,576,015 B2 | | 6/2003 | Geistlich et al. |
| 2003/0171810 A1 | | 9/2003 | Steiner |

FOREIGN PATENT DOCUMENTS

| | | | |
|---|---|---|---|
| FR | 2582517 | 12/1986 | |
| RU | 2104703 | 2/1998 | |
| RU | 2232585 | 7/2004 | |
| RU | 2242981 | 12/2004 | |
| WO | W09844809 | 10/1998 | |
| WO | WO 0119424 A1 * | 3/2001 | ............ A61L 27/36 |

OTHER PUBLICATIONS

International Search Report in PCT/RU2005/000526, dated Jun. 1, 2006.

* cited by examiner

*Primary Examiner* — Rosanne Kosson
(74) *Attorney, Agent, or Firm* — Bardmesser Law Group

(57) ABSTRACT

A biomaterial for osteoplasty has a preserved native spatial organization of collagen matrix and mineral component of bone fabrics of natural origin, for example, containing 25% collagen and 75% mineral substances. The biomaterial is demineralized (compared to original concentration) to contain from 0 to 95% of the original mineral concentration, preferably from 5 to 80%, more preferably from 10 to 60%. The proteins are composed of 99% of collagen and 1% of other proteins. The biomaterial contains bone sulfated glycosaminoglycans (sGAG), whose concentration varies from 0.3 to 3 mg per 1 $cm^3$ of the material. The sGAG is affinity-bound to the bone matrix. The biomaterial may also include bisphosphonates, whose concentration varies from 0.2 to 10 micrograms per 1 gram of material. The biomaterial may also include bone the morphogenetic proteins (BMP), whose concentration varies from 0.001 to 1 micrograms per 1 gram of material.

12 Claims, No Drawings

MATERIAL FOR OSTEOPLASTY AND TISSUE ENGINEERING

CROSS-REFERENCE TO RELATED APPLICATIONS

This application is a continuation in part of U.S. patent application Ser. No. 12/091,741, filed on Apr. 25, 2008, which is a U.S. National Phase of PCT/RU2005/000526, filed on Oct. 27, 2005, which are incorporated by reference herein in their entirety.

BACKGROUND OF THE INVENTION

1. Field of the Invention

This invention covers the field of medicine, in particular, biochemistry and biomaterials extraction technology and is also used for manufacturing of biomaterials applied as a plastic material by the operative restoration of bone defects by destruction of bone tissue, cystectomy, oncotomy and also as a carrier of active substances and drugs, in plastic surgery by restoration of organ's or tissue's volume.

2. Description of the Related Art

A bone is a living tissue, in which a continuous reorganization process including a simultaneous destruction and restoration of the bone material. Old tissue is remodulated during a normal process and also by implantation of a foreign material, new tissue is formed in place of this. Equilibrium is permanently maintained between the quantity of a reformed bone and a newly developed bone. This process will go easier, if the implanted material is close to a natural bone in its structure.

That is why at present it is preferred to prepare the substitute material from tissues of a natural bone, which is normally of animal origin.

It is well-known that a partial demineralization promotes implantation of a bone graft. Hereupon various additional steps are taken, which are intended either for full deproteinization of the bone or for influence onto the nature of proteins remaining bound in the bone base or for increase of this share of proteins.

Methods used heretofore, in particular, U.S. Pat. No. 4,394,370 can be given as an example, where it is proposed to form a spongy mass by melting of a mixture consisting of a powder of the demineralized bone of human origin and a dilutes collagenic powder with the help of glutaraldehydic binding providing a cross-link.

U.S. Pat. No. 4,743,259 combines demineralization by the hydrochloric acid with enrichment by proteins carried out on the first part of the demineralized bone with the help of proteins extracted from the second part with use of guanidine.

Furthermore, FR No. 2,582,517 proposes to process bone ends taken from animals, namely, from livestock by means of a partial demineralization and tanning with use of glutaraldehyde. Bone fragments to be implanted by a surgeon are cut out with necessary shaping from cattle's bones after a preliminary pretreatment including delipidization or defatting operation with use of an organic solvent such as ethanol, demineralization with use of calcium extraction means such as hydrochloric acid and an operation providing for tanning with glutaraldehyde and also various washing operations.

It is obvious from description of patens given above that the mentioned tanning process favours to the features of a treated bone, as it facilitates the cross-linkage of macromolecular chains. However, it is recently detected that the treatment of glutaraldehydes does not result in a significant reduction of immunogenic features and, moreover, the engraftment of the implanted bone occurs in a desirable degree, as opposed to the theory suggested earlier. Furthermore, such chemical compounds like glutaraldehyde have a disadvantage—they are biologically toxic.

A method for obtaining of a material for osteoplasty from the bone issue of natural origin including the subsequent removal of lipids from the natural bone issue with use of an organic solution, selective extraction with the subsequent washing and lyophilization of the end product is known, characterized by that that the selective extraction is carried out with use of the urea solution for denaturation and removal of antigenic proteins with maintaining of a non-denatured collagen of type I in a natural form located in the initial mineral bone structure and the obtained structure is directed to washing and lyophilization (RU Patent No. 2,104,703, publ. Feb. 20, 1998).

At that, the removal of lipids is carried out with use of the organic solution containing 10 volumetric parts of chloroform/methanol or ethanol/dichloromethane mixture per 1 part of bone in proportion of about 2:3-1:3 accordingly. The demineralization of the bone tissue is carried out with the solution of the hydrochloric acid with molarity of 0.1-1.0 M after removal of lipids. The extraction with an ionic solvent is carried out before the selective extraction, in particular, with use of sodium chloride.

The selective extraction is conducted with a 2-10 M urea solution, preferably with a 5-8 M solution or aqueous urea solution containing 0.1-0.5 vol. of mercaptoethanol. The washing is carried out with use of distilled water at 30-60° C., preferably at 45-55° C. Alternatively, the selective extraction is carried out first with use of the urea solution in concentration of 2 to 10 M, preferably 5-8 M, then, after washing,— with use of the aqueous urea solution containing mercaptoethanol in quantity of 0.1-0.5 vol. in the solution.

The material for osteoplasty obtained by such a way represents a compound, in which the bone structure of natural origin containing 20-40% (namely 25-35%) of a non-denaturated collagen of type I is maintained. According to analysis results of dry material, this material contains less than 15% lipids, 25-45% proteins, 10-30% calcium, 5-20% phosphorus and has the water content below 10% and Ca/P ratio in preference from 1 to 2.2.

The material can have a shape of parallelepipedic blocks, truncated pyramids, plates, discs or powder amalgamated with a binder which can be in preference of biological origin such as fibrin or synthetic origin such as, for example, synthetic biodegradable polymer.

This invention is chosen as a prototype both for the method and material, as it is the closest to the proposed invention as regards its engineering solution.

The disadvantage of the mentioned method is the fact that such treatment, although it maintains a bone collagen of type 1 in the natural form, does not provide full removal of antigens—non-collagenic proteins, lipids, lipoproteins and other substances reducing the biocompatibility of the obtained material from this tissue.

SUMMARY OF THE INVENTION

The goal of the invention is to improve the quality of the biomaterial obtained containing hydroxyapatite and/or bone collagen from a bone tissue and to obtain materials for application in stomatology, traumatology and orthopedics on its basis by means of maintaining of the native structure of the bone collagen and spatial organization of the bone tissue for its subsequent cellular colonization, engraftment capacity of such biomaterials at the expense of their antigenic features, to increase the biocompatibility and biointegration.

The technical result reached by use of this invention is the obtaining of a bone biomaterial with maintained architectonics and pure bone collagen being low-antigenic materials, which can be widely used for obtaining of products of medical purpose, such as materials for restoration of bone defects and also as a carrier of active substances and cells and which is able to be a base for other products of medical purpose.

As regards the method, the mentioned technical result is reached by that that the bone is sawn to plates with the thickness of 0.2-2.0 cm, washed with 0.1 M phosphate buffer—ph 5.8-6.0—heated to 65° C., digested in the solution of the activated 0.1-0.4% papain at 65° C. during 24 hours, then the plates are washed with 5 vol. parts of water at 40-80° C. (preferably 50-60° C.), treated with the 0.4 N alkali solution at the room temperature during 10-24 hours, washed with flowing water, defatted in ethanol/chloroform mixtures in proportion of 1:2 and 2:1, decalcified in 0.4-1N hydrochloric acid, treated with 1.5-3% hydrogen peroxide during 4 hours, washed with treated water, then with ethanol, at the room temperature, packed and sterilized.

As regards the material, the technical result is reached by that that the material for osteoplasty and tissue engineering obtained on the basis of this method represents a compound with the native spatial organization of the collagenic matrix and mineral component of the bone tissue of natural origin containing 25% of collagen and 75% of mineral substance. According to analysis results of the dry material, this material contains less than 1% of non-collagenic proteins.

A spongy or cortical bone of human or vertebrates, e.g., pigs, bucks, hens, gooses etc. can serve as a material for obtaining of the bone collagen and products on the basis of this. This tissue mainly consists of collagen of type I and III and is characterized by low solubility and also high resistance to collagenase. This type of the collagen is the most widely used in products of medical purpose being implanted into the organism tissues.

The attributes mentioned both for the method and for the material are essential and interconnected with forming of a stable aggregate of essential attributes sufficient for obtaining of the required technical result.

The technical essence of the method according to this invention and characteristics of the material for osteoplasty and tissue engineering obtained with use of this method are described below.

The use of papain and the subsequent processing of bone tissue permits production of bone fragments where the ratio of primary components (collagen and hydroxyapatite) is about 25% to 75% and is the closest to natural and optimal ration to preserve most physiological parameters of the original (native) bone. The ratio provides for the highest structural strength of the fragments, and the best parameters for binding bone morphogenetic proteins (BMPs). A high concentration of hydroxyapatite in the material permits to slow down the process of degradation of the material after implantation into the organism, i.e., to provide a longer effective influence of the material on inducing bone formation.

A high degree of removal of antigenic components from the bone material (e.g., non-collagenic proteins, lipids and glycoproteins) ensures high performance of the material in terms of biocompatibility and biointegration.

The proposed material can affinity-bind glycosaminoglycans (sGAG) and thereby increase its osteogenic potential significantly. Bone fragments that contain three primary components of bone tissue, such as collegen, hydroxyapatite and sGAG upon implantation can induce ectopic osteogenesis.

Similarly, natural hydroxyapatite in the proposed bone material can affinity bind BMP, whose presence in the material increases its osteogenic properties and its influence on bone marrow stromal cells. The BMPs directly affect other tissue cells, forcing them to alter their chemical exchange properties and differentiate into bone tissue.

Bisphosphonates in water solutions also have a high affinity for hydroxyapatite crystals. Binding to bone hydroxyapatites, the bisphosphanates suppress osteoclast activity, and preserve integrity of the bone and the bone implant. Bisphosphonates stimulate proliferation and osteogenic differentiation of bone marrow stromal cell and thus promote osteoblastic bone formation. The have both direct and indirect influence on osteoblasts.

Thus, the material has high osteogenic properties, high biocompatibility and biointegration properties, a lack of antigenic characteristics, and can be used to replace bone defects as well as a carrier for biologically active pharmaceuticals and cells.

DETAILED DESCRIPTION OF EMBODIMENTS OF THE INVENTION

The process of preparation of bioimplants according to this method requires an initial mechanical treatment of the tissue, when the bone is cleaned free from remainders of soft tissues and blood.

An essential attribute of the invention is the procedure of the bone treatment. After mechanical treatment the tissue is sawed into plates with the thickness not less than about 0.2 cm and not more than about 2.0 cm, as these dimensions are optimal by treatment of this tissue with solutions. The minimum size of plates with the minimum thickness about 0.2 cm and minimum thickness about 2.0 cm are determined by us experimentally. So, difficulties emerge with accessibility of enzyme and other solutions to active places of the substrate and also by washing of such plates free from solutions applied according to this technology by the increase of the plate thickness. Serious problems with maintaining of continuity of the bone collagen and spatial structure of the bone tissue during the material treatment process arise by reduction of the plate thickness.

After cutting, the tissue is washed with the double volume of the 0.1 M phosphate buffer with pH 5.8-6.0 heated to 65° C. Namely washing in the phosphate buffer heated to 65° C. precedes the digesting with the enzyme and creates optimal conditions for subsequent effect of the papain enzyme by sufficient reduction of incubating time with the enzyme by these pH values. The enzyme is able to destroy non-collagenic proteins, proteoglycans and glycoproteins of the bone tissue effectively under these conditions, while fibers of the bone collagen are fully screened with a hydroxyapatite layer and so the bone collagen fibers are not exposed to denaturation and destruction maintaining their native structure by digesting in conditions of increase of temperature up to 65° C. This is clearly seen on the output of sulphated glycosaminoglycans and aminoacids to digest.

Various concentrations of the enzyme can be taken depending on the structure of the bone tissue and its thickness. So, the concentration of 0.1% activated papain is sufficient by the thickness of the spongy bone of 0.2 cm or, in case of treatment of the cortical bone, the papain concentration is increased to 0.4%.

The optimal effect of the papain onto the bone tissue by digesting of proteins and proteoglycans is 24 hours at 65° C. At that, the maximum quantity of non-collagenic proteins and proteoglycans is removed from the bone tissue. It has been found by us experimentally that about 2 g of glycosaminoglycans (sGAG) is extracted to the digest from 1 kg of bones in 24 hours, which is practically equal to the theoretically calculated quantity of sGAG for this type of tissue (Chvapil M., Physiology of connective tissue., Butterworths, London, 1967, p. 67-70).

The bone plates are washed with 5 vol. parts of flowing water heated to 40-80° C. (preferably 50-60° C.) after their digesting with the enzyme. This operation allows to remove all reaction products of the substrate with the enzyme, the enzyme itself and the major part of fats (more than 90%). The effective defatting and removal of possibly remained non-collagenic proterins is reached by the effect of the alkali onto the non-decalcified bone tissue. The treatment of the bone tissue with the 0.4 H NaOH (sodium hydroxide) is carried out during 10-24 hours at the room temperature. It is well-known that the alkali is a very effective agent destructing protein compounds, bacterial and viral particles, with which the bone tissue can be contaminated. This stage must be carried out at the room temperature (18-20° C.), as the efficiency of such effect significantly reduces by the lower temperature and the structure of the collagenic molecule itself and of the collagenic matrix can be destroyed by the temperature increase. As in the case with the enzyme, the initial mineral bone structure covering the collagenic matrix of the bone does not allow the 0.4 H alkali solution to effect on the structure of the bone collagen even after the influence during 24 hours. The spongy bone with the plates size of 0.2-0.5 cm is treated during 10 hours, as protein molecules located on the surface of the collagen fibers are fully destroyed during this period of time. The thicker plates of the spongy bone and fragments of the cortical bone require the effect of alkali during 24 hours.

The protein is not detected in the washouts from the tissue after this time. After treatment with alkali, the bone is washed 5 times in flowing water and the plates are dried at the room temperature.

Unlike known methods of obtaining of biomaterials from the bone, this method proposes to carry out initial treatment—washing and enzymatic influence at high temperatures (65° C.), but at that the destruction of the collagen molecule and collagenic matrix as a whole does not occur. In addition, it is proposed in this method to proceed with defatting and decalcification of the bone after its treatment with enzyme and alkali only, as main antigens are already removed from the non-decalcified bone and the bone collagen remains practically unchanged thanks to a protective layer of hydroxyapatite covering the bone fiber.

A significant quantity of fats and their compounds with proteins and carbohydrates is contained in the bone tissue. The lipids are both in the free state and in form of compounds with sugars—lipopolysaccharides, which are active antigens and can cause various inflammatory complications in the bone plates treated with the enzyme. The method includes the treatment of bone plates in mixtures of chloroform and ethanol in proportion of 2:1 and 1:2 at the stage, when the main bone stroma is already cleaned free from its other components namely for removal of all remained lipids. The treatment in the mixture is carried out twice for about 24 hours in each mixture until the complete removal of lipids, what can be estimated on the basis of the content of fats in 1 g of the dry tissue. This stage allows to ensure the liberation of lipids even from the dense bone tissue (cortical bone).

After such treatment, their output is terminated and the content in the material does not exceed 1%. After defatting the bone plates are dried and decalcified in solutions of mineral acids. As a rule, thin plates of the spongy bone are treated with the 0.4 H solution of hydrochloric acid (HCI), and ticker plates (1 cm and more)—in 1 H HCI and the process is continued until the complete elimination of $Ca^{++}$ ions in the decalcifying solution. The decalcification process of the bone mineral can be not conducted at all or the demineralization degree of the material can be strictly controlled.

The analytical study of the method for obtaining of a material without demineralization has shown that the obtained material has classic showings of the bone tissue: 25% (+/−5%) of collagen and 75% (+/−5%) of mineral substance. At that, not only the structural collagen is not affected, but the spatial organization of the collagenic matrix and mineral component part of the bone tissue remains fully maintained.

The obtained material differs from all materials at present applied in osteoplasty, both in its composition and operating characteristics and also in full absence of non-collagenic components and antigenic features. This material practically fully maintains the native spatial structure of the bone tissue, what is particularly necessary for good integration, biocompatibility and cellular colonization.

Furthermore, this material undergoes treatment with 1.5-3% hydrogen peroxide for about 4 hours. This stage allows first to remove remainders of non-collagenic protein molecules and second to destroy a series of other compounds such as pigments, remained lipids, not readily soluble salts etc. 3% hydrogen peroxide is usually used for treatment of plates with the thickness more than 1.0 cm. The obtained collagen is then washed 5 times in treated water, then in ethanol, dried at the room temperature, packed and sterilized.

The obtaining of the material is controlled at each processing stage and includes main methods accepted for this type of materials.

The absence of proteoglycans was determined on changes in coloration of the substrate and in the solutions spectrophotometrically in the presence of 1.9-dimethylene blue by the wave length of 535 nm based on the Farndel's method.

The protein output was determined based on the Lowry's pharmacopeia method spectroscopically by the wave length of 400 nm. The analysis showed that the concentration of collagen in the total protein fractions in the material was 99%. The amount of collagen in the material determined by the content of hydroxyproline after hydrolysis of dry demineralized protein residue of bone at the 105° C. in 6 N hydrochloric acid by the method of Woessner J F, Jr. ("The determination of hydroxyproline in tissue and protein samples containing small proportions of this amino acid", Arch. Biochem. Biophys., 93, 440, 1961)

The presence of calcium ions in decalcifying solutions was determined with the help of qualitative reaction to $Ca^{2+}$. The control of lipids was carried out by painting the material with Sudan. The structural integrity of the bone collagen was determined by study of histologic sections, electron microscopically and with use of scanning microscopy method. It was established with the help of these methods that the porous-fibrous structure of the bone collagen has a typical appearance without any changes and abnormalities. The control instrumentation was carried out after drying and sterilization for measurement of the content of non-collagenic proteins in the material as compared with the prototype. So, 4-5% of protein is determined per dry weight of the material obtained according to the method described in the prototype and less than 1% —according to the method proposed by us. Thus, the proposed method allows a significant reduction of the material's antigenicity thanks to a more complete removal of non-collagenic proteins as compared with the prototype. Therefore, the proposed method of the tissue treatment allows to maintain the native structure of the material, improve its quality, reduce the materials and thereby ensure good plastic features, biointegration and biocompatibility.

As a result of the process described in this application, a novel biomaterial for osteoplasty and tissue engineering is obtained. The biomaterial has a fully preserved native spatial organization of collagen matrix and mineral component of bone fabrics of natural origin, for example, containing 25% collagen and 75% mineral substances. The biomaterial is demineralized (compared to original mineral concentration) to contain from 0 to 95% of the original (natural) mineral concentration, preferably from 5 to 80%, more preferably from 10 to 60%. The proteins of the material are composed of 99% of collagen and 1% of other proteins.

The biomaterial contains bone sulfated glycosaminoglycans (sGAG), whose concentration varies from 0.3 to 3 mg 1 $cm^3$ of the material, preferably 0.5 to 2.0 mg per 1 $cm^3$ of the material, more preferably from 0.8 to 1.5 mg per 1 $cm^3$ of the material. The sGAG is affinity-bound to the bone matrix. The biomaterial may also include bisphosphonates, whose concentration varies from 0.2 to 10 micrograms per 1 gram of material, preferably 0.4 to 8.0 micrograms per 1 gram of material, more preferably 0.5 to 3 micrograms per 1 gram of material. The biomaterial may also include bone the morphogenetic proteins (BMP), whose concentration varies from 0.001 to 1 micrograms per 1 gram of material, more preferably from 0.05 to 0.4 micrograms per 1 gram of material.

Brief Description of a Process Used for Obtaining of Material

The pig's bone passed a required veterinary control is cleaned from muscles and tendons, sawn up to plates with the thickness of 0.2 cm-2.0 cm and put into the 0.1 M phosphate buffer at 60-70° C., pH 5.6-6.2. The buffer is poured off and the material is washed again with the heated buffer and transferred into the solution of activated 0.4% papain. The incubating is carried out at 60-70° C. in a thermostat for about 20-28 hours. The digest is then poured off and the plates are washed with 5 volumes of water heated to 65-75° C., cooled to the room temperature and put into the 0.3-0.5 H alkali solution for 20-28 hours. The material is washed free from alkali, dried and treated twice—first with the ethanol/chloroform mixture in proportion of 1:2 for about 48 hours and then with the ethanol/chloroform mixture in proportion of 2:1 during the subsequent 48 hours. The bone plates are dried again and put into the 0.9-1.1 N hydrochloric acid. The change of acid is carried out until the complete elimination of calcium ions in the decalcifying solution. The acid is washed with water and the plates are put into a 2.5-3.5% hydrogen peroxide for about 4 hours. Then the plates are washed with the treated water and ethanol, the material is dried, packed and sterilized.

These actions mentioned above lead to reduction of antigenicity and maintaining of the collagenic structure and bone collagenic matrix.

The quantitative and qualitative analysis of the bone collagen is conducted as described above.

The invention is explained on examples of a specific execution for a better essence insight.

Example 1

A donor human bone passed the required analyses is mechanically cleaned from muscles and tendons, sawn up to plates with the thickness of 0.2-0.6 cm and put into the 0.1 M phosphate buffer at 65° C., pH 5.8-6.0 twice for 30 minutes each time. The buffer is then poured off and the plates are transferred into the solution of activated 0.15% papain at 65° C. into the thermostat for 24 hours. Then the supernatant is poured off, the plates are washed with 5 volumes of water at 60° C., cooled to the room temperature and put into the 0.4 H alkali solution for 24 hours. The material is washed free from alkali and dried. The plates are put first into the ethanol/chloroform mixture in proportion of 1:2 twice for 4 hours and then twice into the same mixture but in proportion of 2:1 for 24 hours. The material is dried and treated with the 1.5% hydrogen peroxide during 4 hours. Then the plates are washed first with the treated water and then with ethanol.

In case of obtaining of a bone collagen, the material is dried after its defatting in organic solutions and decalcified in the 0.5 N hydrochloric acid. The acid is washed out and the bone plates are treated with the 1.5% hydrogen peroxide during 4 hours. Then the material is washed again first with the treated water and then with ethanol. The material treated with use of such method is dried at the room temperature, frozen-dried, packed and sterilized with use of radiation method. Bones of animals with the thickness of up to 0.8 cm are treated in a similar manner.

The analytic study with respect to the presence of proteins, proteoglycans and lipids in the material is conducted at the end of each technological cycle. The obtained materials are applied for restoration of bone defects by operative intervention in stomatology, orthopedics and traumatology. The non-decalcified bone material and bone collagen can be saturated with bioactive substances (sulfated glycosaminoglycans, bisphosphonates, growth factors—BMP, PDGF, IGF, FGF etc. for clinical, experimental and scientific purposes and also can be used as carriers for various types of cells—stem, embryonic, blood cells etc.

Example 2

The pig's spongy bone passed a required veterinary control is mechanically cleaned from muscles and tendons, sawn up to plates with the thickness of 1.1-2.0 cm and put into the 0.1 M phosphate buffer at 65° C., pH 5.8-6.0 twice for 60 minutes each time. The buffer is then poured off and the plates are transferred into the solution of activated 0.3% papain at 65° C. into the thermostat for 24 hours. Then the digest is poured off, the plates are washed with 5 volumes of water at 70° C., cooled and put into the 0.4 H alkali solution at the room temperature for 24 hours.

The material is washed free from alkali and dried. The plates are put first into the ethanol/chloroform mixture in proportion of 1:2 twice for 4 and 24 hours and then twice into the same mixture but in proportion of 2:1 for the subsequent 4 and 24 hours. After defatting, the material is dried and treated immediately with the 3.0% hydrogen peroxide during 4 hours or decalcified in the 1 N hydrochloric acid and then treated with the 3.0% hydrogen peroxide during 4 hours with the following washing free from the acid. Both kinds of material are washed first with treated water and then with ethanol. The bone matrix and bone collagen obtained by such a way are cut to fragments of various shape and size: cubes, parallelepipeds, blocks etc. and dried at the room temperature or with use of the lyophilic method, packed and sterilized by radiation. Bones of various animals and humans with the thickness exceeding 1 cm are treated in a similar manner.

The analytical study with respect to the presence of proteins, proteoglycans and lipids in the material is conducted at the end of each technological cycle. The obtained materials are applied for restoration of bone defects by operative intervention in stomatology, orthopedics and traumatology. The non-decalcified bone material and bone collagen can be saturated with bioactive substances (sulfated glycosaminoglycans, bisphosphonates, growth factors—BMP, PDGF, IGF, FGF etc. for clinical, experimental and scientific purposes and also can be used as carriers for various types of cells—stem, embryonic cells etc.

Example 3

The pig's cortical bone passed a required veterinary control is mechanically cleaned from muscles and tendons, sawn up to plates with the 10 thickness of 1.5-2.0 cm and put into the 0.1 M phosphate buffer at 65° C., pH 5.8-6.0 twice for 60 minutes each time. The buffer is then poured off and the plates are transferred into the solution of activated 0.4% papain at 65° C. into the thermostat for 24 hours. Then the digest is poured off, the plates are washed with 5 volumes of water at 80° C., cooled and put into the 0.4 N alkali solution at the room temperature for 24 hours.

The material is washed free from alkali and dried. The plates are put first into the ethanol/chloroform mixture in proportion of 1:2 twice for 4 and 24 hours and then twice into the same mixture but in proportion of 2:1 for the subsequent 4 and 24 hours. As in the previous example, the material is dried and treated immediately with the 3.0% hydrogen peroxide during 24 hours (osteomatrix) or decalcified in the 1 N hydrochloric acid and only then treated with the 3.0% hydrogen peroxide during 24 hours after washing free from the acid (bone collagen). Both kinds of material are washed first with the treated water and then with ethanol.

The biomaterials obtained in such a way are cut into fragments of various shape and size: cubes, parallelepipeds, disks, blocks etc. and dried at the room temperature, packed and sterilized by radiation. Bones of various animals and humans with the thickness exceeding 1 cm are treated in a similar manner. The analytical study with respect to the presence of proteins, proteoglycans and lipids in the material is conducted at the end of each technological cycle. The obtained materials are applied for restoration of bone defects by operative intervention in stomatology, orthopedics and traumatology. The non-decalcified bone material and bone collagen can be saturated with bioactive substances (sulfated glycosaminoglycans, bisphosphonates, growth factors—BMP, PDGF, IGF, FGF etc. for clinical, experimental and scientific purposes and also can be used as carriers for various types of cells—stem, embryonic cells etc.

Example 4

A donor human bone passed the required analyses is mechanically cleaned from muscles and tendons, sawn up to plates with the thickness of 0.5-0.8 cm and is treated as per example 1 until the decalcification stage. Then defatted bone plates are dried and treated with the 1.5% hydrogen peroxide during 6 hours. The plates are washed first with the treated water and then with ethanol. The material treated by such a way is dried at the room temperature, frozen-dried, packed and sterilized by radiation. Bones of animals with the thickness of 0.5-1.0 cm are treated in a similar manner.

The analytical study with respect to the presence of proteins, proteoglycans and lipids in the material is conducted at the end of each technological cycle.

Example 5

The pig's spongy or cortical bone passed a required veterinary control is mechanically cleaned from muscles and tendons, sawn up to plates with the thickness of 1.0-2.0 cm and then treated as per example 2 until the decalcification stage. Then defatted bone plates are dried and treated with the 1.5% hydrogen peroxide during 6 hours. The plates are washed first with the treated water and then with ethanol. The material treated by such a way is dried at the room temperature, frozen-dried, packed and sterilized ethanol. Bones of animals with the thickness of 0.5-1.0 cm are treated in a similar manner.

INDUSTRIAL APPLICABILITY

This invention is industrially applicable, mastered in vitro, the laboratory results show the practical value of the obtained material for osteoplasty and tissue engineering.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

What is claimed is:

1. A material for osteoplasty comprising:
   a dry bone fragment formed of a natural collagen matrix and hydroxyapatite, wherein the collagen matrix and the hydroxyapatite are from natural bone tissue, the material having the natural spatial organization of the collagen matrix and the hyroxyapaptite of the bone tissue of natural origin; the dry bone fragment having about 25% of collagen and about 75% of hydroxyapatite, wherein the material in its dry form comprises less than 1% of non-collagenic proteins.

2. The material of claim 1, wherein the material includes sulfated glycosaminoglycans (sGAG) that are affinity bound to the collagen matrix.

3. The material of claim 2, wherein the concentration of sGAG varies from 0.3 to 3 mg per 1 $cm^3$ of the material.

4. The material of claim 2, wherein the concentration of sGAG varies from 0.5 to 2.0 mg per 1 $cm^3$ of the material.

5. The material of claim 2, wherein the concentration of sGAG varies from 0.8 to 1.5 mg per 1 $cm^3$ of the material.

6. The material of claim 1, wherein the material includes bisphosphonates.

7. The material of claim 6, wherein the concentration of the bisphosphonates varies from 0.2 to 10 micrograms per 1 gram of the material.

8. The material of claim 6, wherein the concentration of the bisphosphonates varies from 0.4 to 8.0 micrograms per 1 gram of the material.

9. The material of claim 6, wherein the bisphosphonates include Zoledronate in a concentration of 0.5 to 3 micrograms per 1 gram of the material.

10. The material of claim 1, wherein the material includes bone morphogenetic proteins (BMPs).

11. The material of claim 10, wherein the concentration of the BMP varies from 0.001 to 1 micrograms per 1 gram of the material.

12. The material of claim 10, wherein the concentration of the BMP varies from 0.05 to 0.4 micrograms per 1 gram of the material.

* * * * *